(12) United States Patent
Fu et al.

(10) Patent No.: US 8,663,946 B2
(45) Date of Patent: Mar. 4, 2014

(54) METHOD AND KIT FOR DETECTING FOLATE

(75) Inventors: Tzu-Fun Fu, Tainan (TW); Tseng-Ting Kao, Kaohsiung (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/372,107

(22) Filed: Feb. 13, 2012

(65) Prior Publication Data

US 2012/0208220 A1 Aug. 16, 2012

(30) Foreign Application Priority Data

Feb. 14, 2011 (TW) .............................. 100104771 A

(51) Int. Cl.
*C12Q 1/26* (2006.01)
*C12N 9/00* (2006.01)

(52) U.S. Cl.
USPC .............. 435/25; 435/183; 435/189; 435/212

(58) Field of Classification Search
None
See application file for complete search history.

(56) References Cited

U.S. PATENT DOCUMENTS

2004/0043441 A1 3/2004 Dervieux et al.

OTHER PUBLICATIONS

Tseng-Ting Kao, et al., "Characterization and Comparative Studies of Zebrafish and Human Recombinant Dihydrofolate Reductases—Inhibition by Folic Acid and Polyphenols", Drug Metabolish and Disposition, vol. 36, No. 3; The American Society for Pharmacology and Experimental Therapeutics, pp. 508-516, (2008).

Tseng-Ting Kao, et al., "Recombinant Zebrafish γ—Glutamyl Hydrolase Exhibits Properties and Catalytic Activities Comparable with Those of Mammalian Enzyme", Drug Metabolism and Disposition, vol. 37, No. 2; The American Society for Pharmacology and Experimental Therapeutics, pp. 302-309, (2009).

Tseng-Ting Kao, et al., "Grape seed extract inhibits the growth and pathogenicity of *Staphylococcus aureus* by interfering with dihydrofolate reductase activity and folate-mediated one-carbon metabolism", International Journal of Food Microbiology, 2010; Elsevier, pp. 17-27.

Wen-Ni Chang, et al., "Cloning expression, purification, and characterization of zebrafish cytosolic serine hydroxymethyltransferase", Protein Expression and Purification; 2006; Elsevier, pp. 212-220.

Robert F. Doherty and Gary R. Beecher,A method for analysis of natural and synthetic folate in foods, Journal of Agricultural and Food Chemistry, 2003, p. 354-361, American Chemical Society.

Chao Wang, Ken M. Riedl, Steven J. Schwartz, A liquid chromatography-tandem mass spectrometric method for quantitative determination of native 5-methyltetrahydrofolate and its polyglutamyl derivatives in raw vegetables, Journal of Chromatography B, 2010, p. 2949-2958, Elsevier.

*Primary Examiner* — Nashaat Nashed
(74) *Attorney, Agent, or Firm* — Muncy, Geissler, Olds & Lowe, P.C.

(57) ABSTRACT

A method and a kit for detecting folate are disclosed. The method includes the following steps: (a) mixing a sample and an extraction buffer to form a mixture, heating and then cooling the mixture, and separating a supernatant from the mixture by centrifugation; (b) adding a recombinant γ-glutamyl hydrolase (GGH) and a folate conversion enzyme to the supernatant to drive catalysis; (c) stopping the catalysis; and (d) analyzing the supernatant by high performance liquid chromatography.

5 Claims, 5 Drawing Sheets

METHOD AND KIT FOR DETECTING FOLATE

CROSS REFERENCE TO RELATED APPLICATION

This application claims the benefits of the Taiwan Patent Application Serial Number 100104771, filed on Feb. 14, 2011, the subject matter of which is incorporated herein by reference.

BACKGROUND OF THE INVENTION

1. Field of the Invention

The present invention relates to a method and a kit for detecting folate and, more particularly, to a method and a kit for rapidly and safely detecting folate.

2. Description of Related Art

Folic acid (folate) is an essential vitamin. In cells, it is often reduced into dihydrofolate (DHF) and tetrahydrofolate (THF), the biologically active forms. Additional glutamate residues are then added to form folyl polyglutamates. THF carries chemically activated one-carbon units (1-C) on N-5 and/or N-10 positions and these one-carbon units are required for the biosynthesis of many important molecules such as nucleic acids, amino acids, proteins, neurotransmitters, and some other vitamins. Therefore, THF plays an important role in the metabolism of these molecules. In addition, deficiency of folate has been implicated in many pathological conditions including neural tube defects (NTDs), cancer and cardiovascular diseases.

Generally, mammals are unable to synthesize folate and are, therefore, mostly dependent on their food supply for this vitamin. However, folate is very unstable and easily destroyed in the cooking process. This might be one of the reasons why folate deficiency occurs more often than any other vitamin deficiency in humans.

High performance liquid chromatography (HPLC) is commonly used for folate detection. Before HPLC analysis, [glutamate]$_n$ of folyl polyglutamates has to be removed from a sample. At present, a large amount of addition of animal serum or tissue extracts is executed to remove [glutamate]$_n$ in most traditional methods.

In the aforesaid methods, processing a sample approximately takes several hours or up to tens of hours. However, a large amount of folate is degraded owing to its instability and thermolability during the aforementioned process, resulting in a great loss of folate. Furthermore, a large amount of addition of animal serum or tissue extracts makes the sample diluted and then influences reliability of the test results as well as increasing the risk of infecting lab operators.

Therefore, it is desirable to provide a new method for detecting folate to overcome the above drawbacks and to identify the amount and the ratio of different folate derivatives in a tested sample.

SUMMARY OF THE INVENTION

The object of the present invention is to provide a method for detecting folate. The method is able to achieve a purpose of detecting folate within a short period of time and to detect folate derivatives that are undetectable in traditional methods. Furthermore, the use of animal serum or tissue extracts is avoided to decrease the risk of biological infection and to increase accuracy and reproducibility in the method.

To achieve the object, the present invention provides a method for detecting folate, comprising the following steps: (a) mixing a sample and an extraction buffer to form a mixture, heating and then cooling the mixture, and separating a supernatant from the mixture by centrifugation; (b) adding a recombinant γ-glutamyl hydrolase (GGH) and a folate conversion enzyme to the supernatant to drive catalysis; (c) stopping the catalysis; and (d) analyzing the supernatant by high performance liquid chromatography to quantify the folate.

In one aspect of the method according to the present invention, the extraction buffer of step (a) is weakly acidic and contains an antioxidant; the extraction buffer of step (a) can be 6-10 times the volume of the sample; and the extraction buffer and the sample can be boiled before the centrifugation in step (a).

In another aspect of the present invention, the folate conversion enzyme can be one or more selected from a group consisting of dihydrofolate reductase (DHFR), 10-formyltetrahydrofolate dehydrogenase (FDH), N-terminal domain of FDH, and a combination of serine hydroxymethyl-transferase (SHMT) and methylenetetrahydrofolate dehydrogenase (MTD). In addition, the method can further comprise adding a reductive nicotinamide adenine dinucleoside phosphate (NADPH) to the supernatant of step (b).

The aforementioned folate conversion enzyme acts pursuant to the following Formulae I to IV.

(Formula I)

(Formula II)

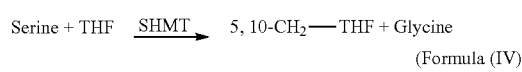
(Formula III)

(Formula IV)

In the method of the present invention, the detectable folate can be, for example, dihydrofolate (DHF), tetrahydrofolate (THF), 5-methyltetrahydrofolate (5-CH$_3$-THF) and 10-formyltetrahydrofolate (10-CHO-THF).

Another object of the present invention is to provide a kit for detecting folate. The kit is a convenient tool for lab operators to detect folate and is helpful to decrease the time of detection. In addition, the risk of biologically infecting lab operators is reduced since folate is detected with the kit but not with animal serum or tissue extracts. Accordingly, the safety, accuracy, and reproducibility of detection can be improved.

In order to achieve the object above, the present invention further provides a kit for detecting folate, comprising: an extraction buffer; a recombinant γ-glutamyl hydrolyze; and a folate conversion enzyme.

In one aspect of the kit according to the present invention, the folate conversion enzyme can be one or more selected from a group consisting of dihydrofolate reductase (DHFR), 10-formyltetrahydrofolate dehydrogenase (FDH), N-terminal domain of FDH, and a combination of serine hydroxymethyl-transferase (SHMT) and methylenetetrahydrofolate dehydrogenase (MTD). Additionally, the kit can further comprise a reductive nicotinamide adenine dinucleoside phosphate (NADPH).

In another aspect of the kit according to the present invention, the extraction buffer can be weakly acidic and contain an antioxidant; the detectable folate can be, for example, one or more selected from a group consisting of dihydrofolate (DHF), tetrahydrofolate (THF), 5-methyltetrahydrofolate (5-CH$_3$-THF) and 10-formyltetrahydrofolate (10-CHO-THF).

In the present invention, purified enzymes obtained from monoclonal techniques are used to efficiently reduce the time of processing a sample to 30 minutes or less. Thus, degradation, loss, and destruction of folate during the process are considerably decreased. In the meantime, the folate enzymes specifically convert the substrates into the corresponding products. Hence, the accuracy and reliability of HPLC to recognize folate from the processed sample can be improved, and the signals of some relatively unstable and undetectable folate derivatives can be further augmented. Accordingly, various folate derivatives that are not detectable in the current traditional methods can be rapidly detected and quantified.

DETAILED DESCRIPTION OF THE PREFERRED EMBODIMENT

Method for Processing Samples

Figure 1A:
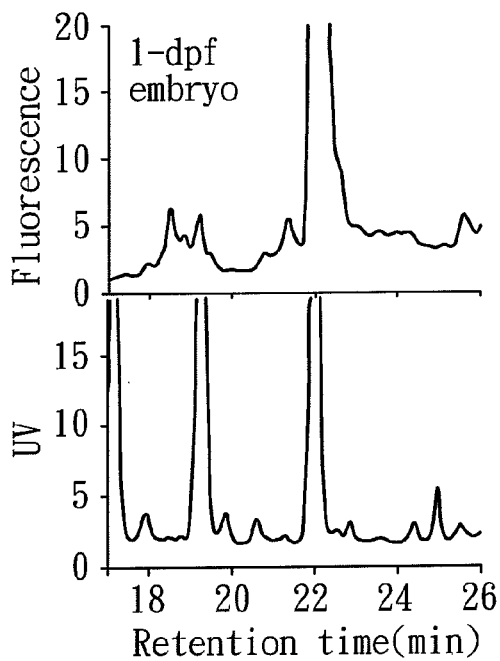
FIG. 1 shows the result of folate detection of zebrafish eggs and embryos in Example 1 of the present invention, in which (A) shows HPLC fluorescence and UV chromatograms of the extract of an embryo at 1 day post-fertilization (1-dpf) that is incubated with no enzymes, (B) shows HPLC fluorescence and UV chromatograms of the embryo (1-dpf) extract that is incubated with GGH, (C) shows HPLC fluorescence and UV chromatograms of the embryo (1-dpf) extract that is incubated with GGH and DHFR, (D) shows HPLC fluorescence and UV chromatograms of the embryo (1-dpf) extract that is incubated with GGH and FDH, (E) shows HPLC fluorescence and UV chromatograms of the embryo (1-dpf) extract that is incubated with GGH, SHMT and MTD, and (F) shows the amounts of THF, 10-CHO-THF, DHF and 5-CH3-THF in the extracts of zebrafish eggs and embryos at 1-, 3-, and 5-dpf.
Figure 1B:
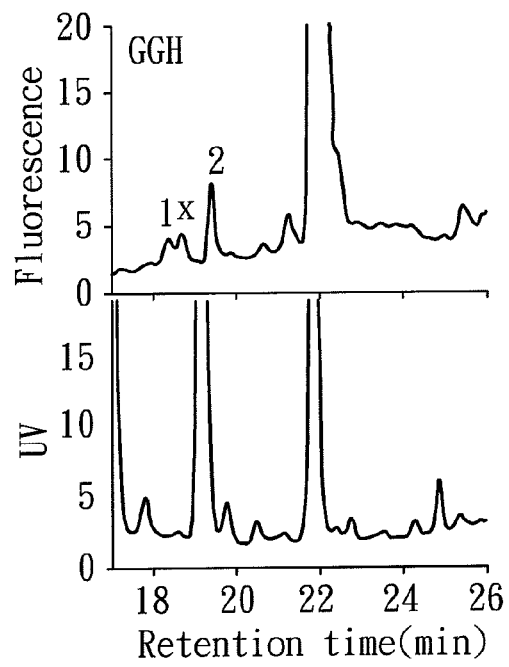
Figure 1C:
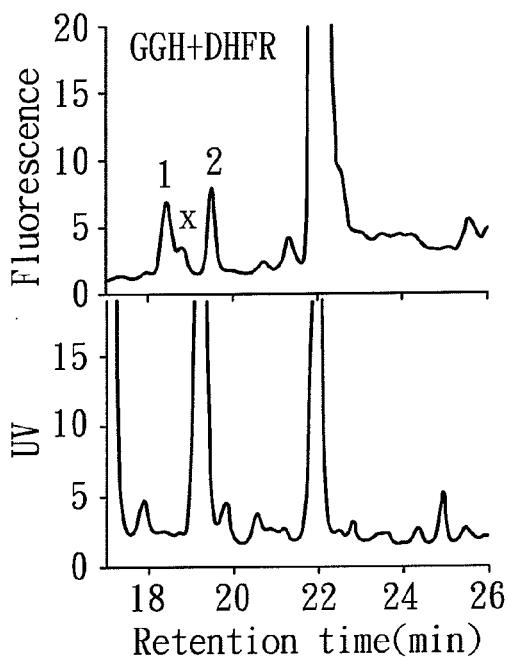
Figure 1D:
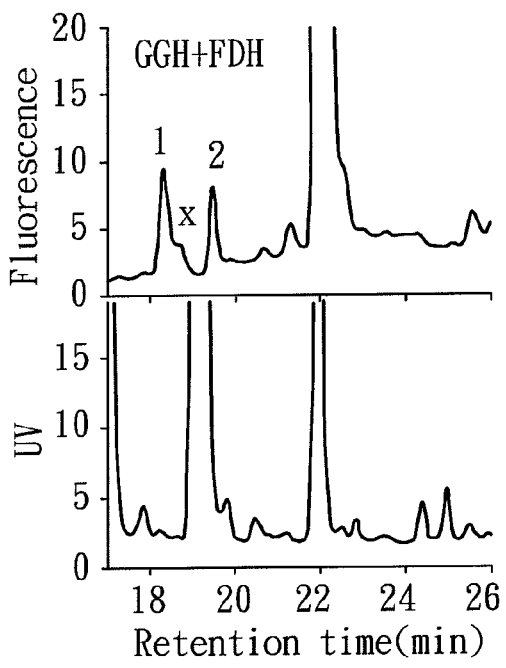
Figure 1E:
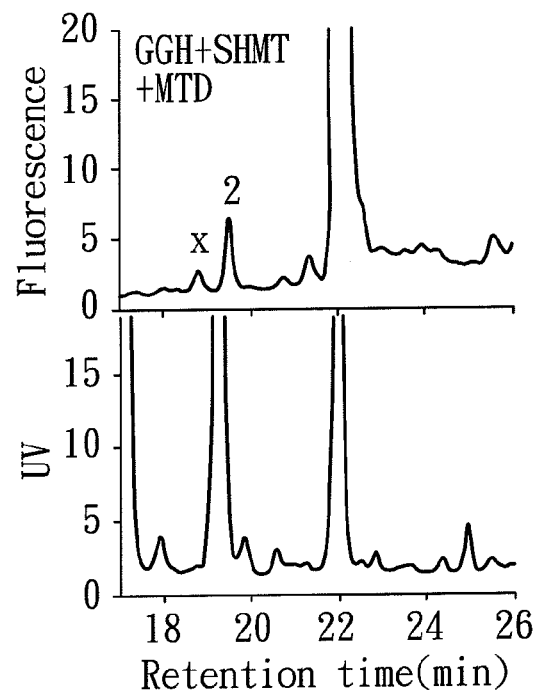
Figure 1F:
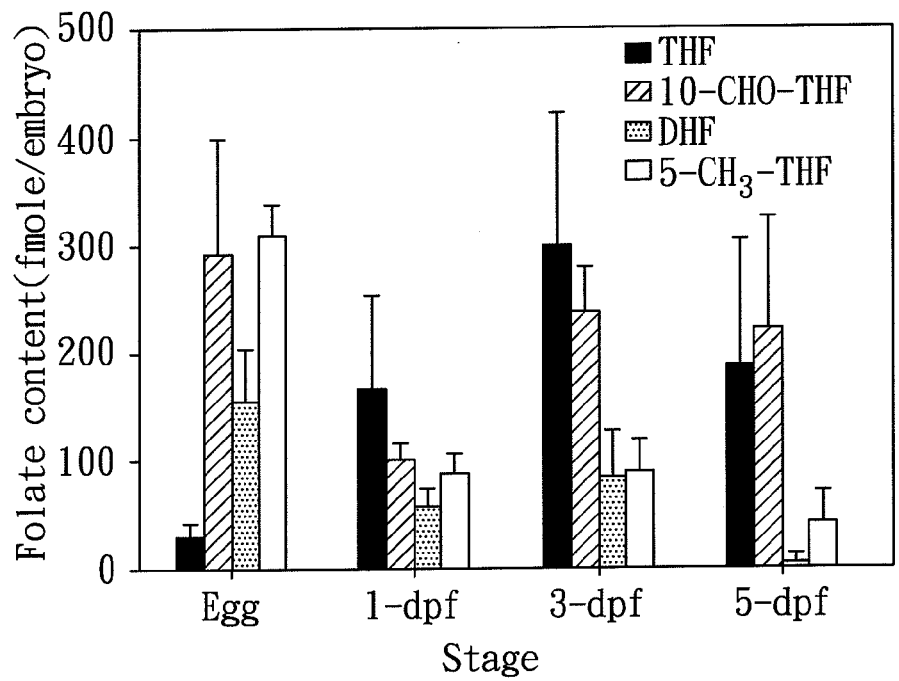
Figure 2A:
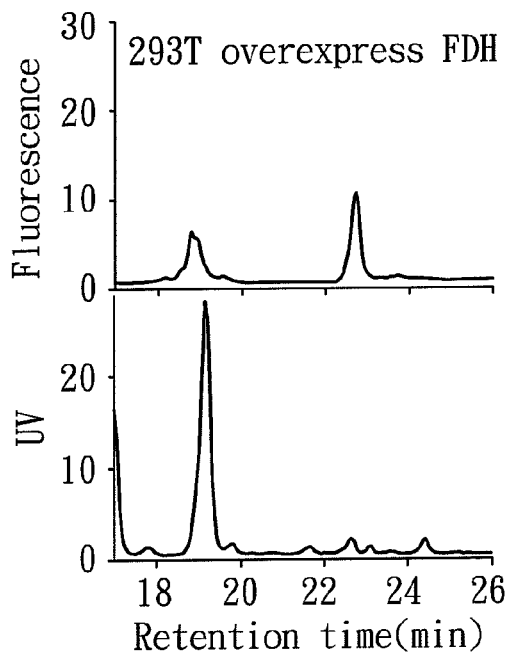
FIG. 2 shows the result of folate detection of human 293T cells in Example 2 of the present invention, in which (A) shows HPLC fluorescence and UV chromatograms of an extract of human 293T cells which is not incubated with enzymes, (B) shows HPLC fluorescence and UV chromatograms of human 293T cell extracts that are incubated with GGH, (C) shows HPLC fluorescence and UV chromatograms of human 293T cell extracts that are incubated with GGH and DHFR, (D) shows HPLC fluorescence and UV chromatograms of human 293T cell extracts that are incubated with GGH and FDH, (E) shows HPLC fluorescence and UV chromatograms of human 293T cell extracts that are incubated with GGH and MTD, and (F) shows HPLC fluorescence and UV chromatograms of human 293T cell extracts that are incubated with GGH, SHMT and MTD.
Figure 2B:
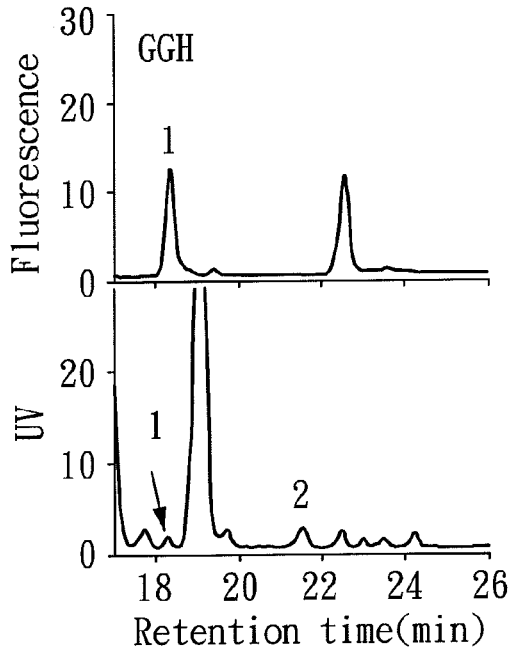
Figure 2C:
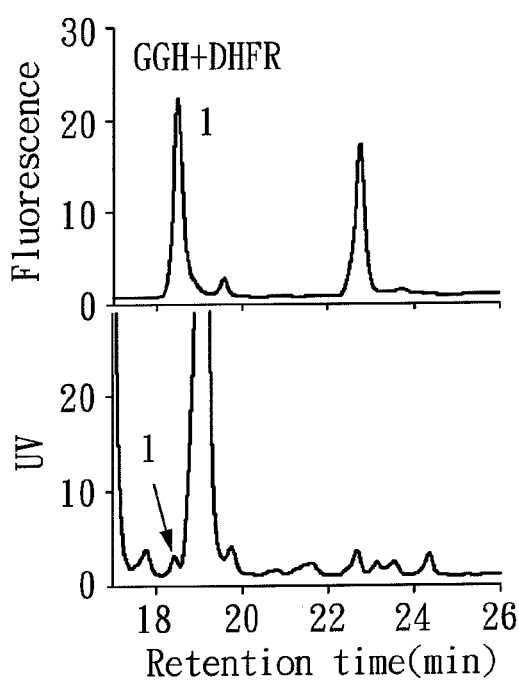
Figure 2D:
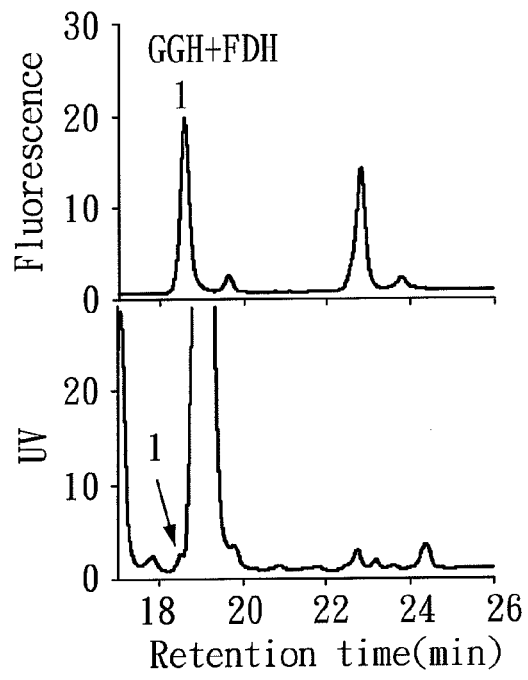
Figure 2E:
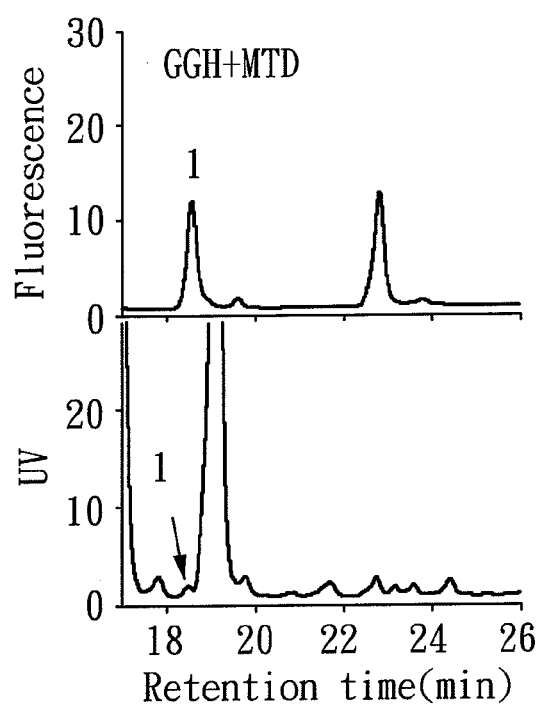
Figure 2F:
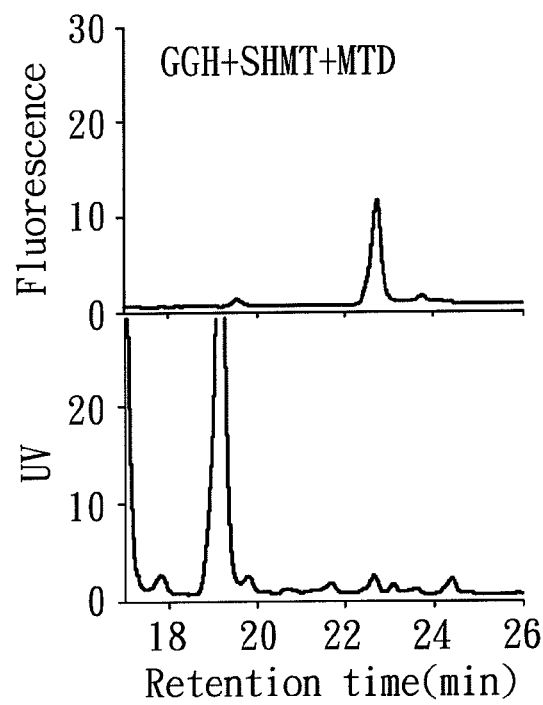

First, samples were homogenized with 6-10 times the volume of the extraction buffer containing ascorbate that was used as an antioxidant. Subsequently, the homogenates were boiled for 3-10 minutes and then immediately cooled on ice. The inventors of the present invention found that excessively long boiling time destroyed some folate derivatives. For example, when the boiling time was extended to 20 minutes, an approximate 50% decrease was observed for DHF amount.

Then, the chilled homogenates were centrifugated at high speed to remove debris. The clear supernatants were transferred to a clean tube, and a recombinant γ-glutamyl hydrolase (GGH) and a folate conversion enzyme as desired were added to the supernatant. The mixtures were incubated at 35-40° C. for 3-10 minutes before heat inactivation. In the enzymatic reactions, folyl polyglutamates were converted into monoglutamate forms by GGH. For example, triglutamates of 5-CHO-THF and pentaglutamates of methotrexate can be converted into corresponding monoglutamate forms.

Finally, the reacted mixtures were centrifugated and filtrated to afford the supernatant for HPLC analysis. The aforesaid extraction buffer was 0.1 M phosphate buffer containing 2% ascorbate and 0.1% 2-mercaptalethanol at pH 6.0. However, the extraction buffer of the present invention was not limited thereto. One skilled in the art of the present invention can adjust the components and pH value of the buffer according to the sorts of the samples to be processed and other related considerations. Generally, the pH value of the extraction buffer was optimized at approximately 5-7.

HPLC Analysis

HPLC system (Agilent 1100) was equipped with Aquasil C$_{18}$ column (150×4.6 mm, 3 μm, Thermo Electron Corporation, USA) and fluorescence detector ($\lambda_{ex}$=290 nm and $\lambda_{em}$=360 nm). The column was equilibrated with 6% solvent B (94% solvent A) at the flow rate of 0.4 ml/min, and solvents A and B were 30 mM phosphoric acid (pH 2.3) and acetonitrile, respectively.

The supernatant (50 μl) to be analyzed was injected into the equilibrated column and then the column was eluted with 6% solvent B for min. Over the next 20 min, solvent B was linearly increased to 25% and held at this level for an additional 2 min. After that, the solvent composition was decreased to 6% solvent B in 1 min and the column was equilibrated for an additional 20 min before the next sample injection.

Establishment of Standard Curve

Fluorescent folate derivatives such as THF, which emit strong fluorescence, were used to establish an HPLC standard curve for the quantification of fluorescent folates in various samples.

Quantification of Various Folates

Except for those emitting fluorescence described above, folate derivatives such as DHF and 10-CHO-THF, which did not emit fluorescence, were converted into THF by folate conversion enzymes such as DHFR. Hence, the peaks of these folate derivatives could be identified on HPLC chromatograms (i.e. the retention time of the peaks) and the intensity of the signals could also be enhanced.

For quantification of 10-CHO-THF in samples, FDH (or N-terminal domain of FDH having activity of hydrolase) was used as the folate conversion enzyme to convert 10-CHO-THF into THF.

The increased amount of THF was calculated by determining the increased THF peak area ($A_{after\ FDH\ conversion} - A_{without\ FDH\ conversion}$) with the THF standard curve so as to quantify 10-CHO-THF.

Unexpectedly, the inventors of the present invention found that during the conversion of 10-CHO-THF into THF by GGH and FDH, some complicated causes made the drop of THF peak occur in the THF standards and the intensity of the drop increased as the amount of THF increased. In order to overcome this problem, pure THF was added to each sample until the final concentration of THF reached 120 nM prior to enzymatic conversion. Under these conditions, the response of standards containing increasing amounts of 10-CHO-THF was linear with a 53% recovery rate. Because the approximately 50% recovery of 10-CHO-THF was found in control experiments, in order to correct experimentally obtained amounts, the increase in the THF peak area from experimental studies was multiplied by 2 to give the total amount of 10-CHO-THF in the sample.

The aforesaid method was also used to correct the experimentally obtained amounts of DHF. Because an approximately 30% recovery of DHF was found in control experiments, the increased amount of THF calculated by the increased THF peak area ($A_{after\ DHFR\ conversion} - A_{without\ DHFR\ conversion}$) according to the THF standard curve was multiplied by 3 to give the total amount of DHF in the sample.

Because of the specific embodiments illustrating the practice of the present invention, one skilled in the art can easily understand other advantages and efficiency of the present invention through the content disclosed herein. The present invention can also be practiced or applied by other variant embodiments. Many other possible modifications and variations of any detail in the present specification based on different outlooks and applications can be made without departing from the spirit of the invention.

EXAMPLE 1

Zebrafish Eggs and Embryos

Zebrafishes (*Danio rerio*, AB strain) were bred and maintained in a 10-14 hour light-dark diurnal cycle. Briefly, 50 zebrafish eggs or embryos at indicated stages were collected, homogenized and ultra-sonicated in 0.3 ml of extraction buffer flushed with nitrogen. The clear lysates were heated in boiling water for 5 min, cooled, and then centrifugated. The supernatants (100-200 µl) were incubated with no enzyme (A) or with others as follows:

(B) 1 µl GGH (4 µg/µl, obtained according to Kao T.-T. et al, *Drug Metabolism and Disposition*, 2009, 37 (2): 302-309);

(C) 1 µl GGH (4 µg/µ 1) and 5 µg DHFR (obtained according to Kao T-.T. et al, *Drug Metabolism and Disposition*, 2008, 36 (3): 508-516);

(D) 1 µl GGH (4 µg/µl) and 5 µg FDH (obtained according to Kao T.-T. et al, *International Journal of Food Microbiology*, 2010, 141: 17-27); or (E) 1 µl GGH (4 µg/µl ), 3 µg MTD (its clone from Virginia Commonwealth University, Richmond, Va., USA, Dr. Verne Schirch) and 6 µg SHMT (obtained according to Chang W.-N. et al, *Protein Expression and Purification*, 2006, 46: 212-220).

Then, the mixtures were incubated at 37° C. for 5 minutes, boiled for 3 minutes to stop enzymatic reaction, centrifugated, and then filtrated. The obtained supernatants were analyzed by HPLC.

The results are shown in FIG. 1. In FIG. 1, (A) shows HPLC fluorescence and UV chromatograms of the embryo (1-dpf) extract that is not incubated with enzymes, (B) shows HPLC fluorescence and UV chromatograms of the embryo (1-dpf) extract that is incubated with GGH, (C) shows HPLC fluorescence and UV chromatograms of the embryo (1-dpf) extract that is incubated with GGH and DHFR, (D) shows HPLC fluorescence and UV chromatograms of the embryo (1-dpf) extract that is incubated with GGH and FDH, (E) shows HPLC fluorescence and UV chromatograms of the embryo (1-dpf) extract that is incubated with GGH, SHMT and MTD, and (F) shows the amounts of THF, 10-CHO-THF, DHF and 5-$CH_3$-THF in the extracts of zebrafish eggs and embryos at 1-, 3-, and 5-dpf. In the HPLC chromatograms, 1 represents THF/5, 10-$CH_2$-THF, 2 represents 5-$CH_3$-THF, and X represents an unknown compound.

Based on the above, zebrafish embryos at different stages of development have extremely different sorts and amounts of folates. In addition to 5-$CH_3$-THF, unfertilized eggs also contain 10-CHO-THF in a large amount. During the development, the amount of 5-$CH_3$-THF decreases but that of THF increases. In embryos, the change of the relative concentrations among various folate derivatives probably has influence on the activity of folate enzymes and cell physiology.

EXAMPLE 2

Human 293T Cells

Cultured human 293T cells of FDH overexpression were harvested (approximately $1 \times 10^6$) and briefly washed with Phosphate buffered saline (PBS). Subsequently, according to the manner of Example 1, the cells were mixed with the extraction buffer, ultra-sonicated, heated, cooled, and then centrifugated. The supernatant (100-200 µl) was incubated with no enzyme (A) or with others as follows:

(B) 1 µl GGH (4 µg/µl);
(C) 1 µl GGH (4 µg/µl) and 5 µg DHFR;
(D) 1 µl GGH (4 µg/µl) and 5 µg FDH;
(E) 1 µl GGH (4 µg/µl) and 3 µg MTD; or
(F) 1 µl GGH (4 µg/µl), 3 µg MTD, and 6 µg SHMT.

Then, the mixtures were incubated at 37° C. for 5 minutes, boiled for 3 minutes to stop enzymatic reaction, centrifugated, and then filtrated. The obtained supernatants were analyzed by HPLC.

The results are shown in FIG. 2. In FIG. 2, (A) shows HPLC fluorescence and UV chromatograms of an extract of human 293T cells which is not incubated with enzymes, (B) shows HPLC fluorescence and UV chromatograms of human 293T cell extracts that are incubated with GGH, (C) shows HPLC fluorescence and UV chromatograms of human 293T cell extracts that are incubated with GGH and DHFR, (D) shows HPLC fluorescence and UV chromatograms of human 293T cell extracts that are incubated with GGH and FDH, (E) shows HPLC fluorescence and UV chromatograms of human 293T cell extracts that are incubated with GGH and MTD, and (F) shows HPLC fluorescence and UV chromatograms of human 293T cell extracts that are incubated with GGH, SHMT and MTD. In the HPLC chromatograms, 1 represents THF/5, 10-$CH_2$-THF, 2 represents 10-CHO-THF, and X represents an unknown compound.

Based on the above, the method of the present invention can sensitively detect slight changes of the intracellular folate pool. For example, overexpression of FDH generally makes the amount of various folate derivatives including 10-CHO-THF (i.e. the substrate of FDH) increase in the cells. This indicates FDH may be a protein serving storage of folates.

COMPARATIVE EXAMPLE

*Staphylococcus aureus*

*S. aureus* was cultured until the log phase, seeded in tryptic soy broth (TSB) with or without 1 mg/ml grapefruit seed extract (GSE), and then incubated at 37° C. for 6-8 hours. The broth (12 ml) was centrifugated and the pellet was collected. Subsequently, in accordance with the manner of Example 1, the pellet was suspended in the extraction buffer (4 ml), ultra-sonicated for 30 seconds, heated for 10 minutes, cooled, and centrifugated. The supernatant (60 µl) was mixed with 1 µl GGH (1 µg/µl), incubated at 37° C. for 5 minutes, boiled for 3 minutes to stop enzymatic reactions, and then filtrated. The clear supernatant was analyzed by HPLC.

Figure 3A:
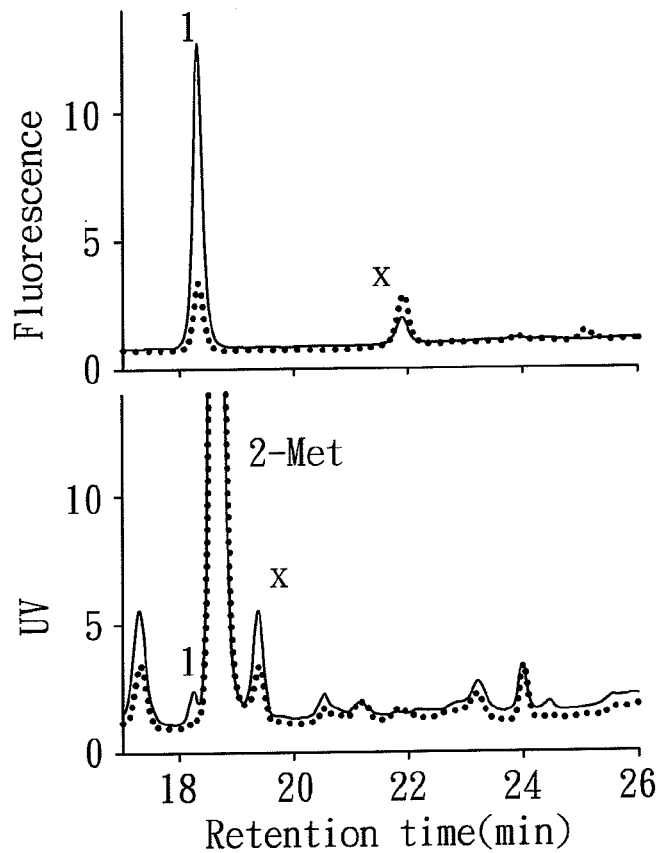
FIG. 3 shows the result of folate detection of *Staphylococus aureus* in Comparative Example of the present invention, in which (A) shows HPLC fluorescence and UV chromatograms of *S. aureus* and solid and dotted lines respectively represent without or with grapefruit seed extract (GSE), and (B) shows a bar chart of THF content.
Figure 3B:
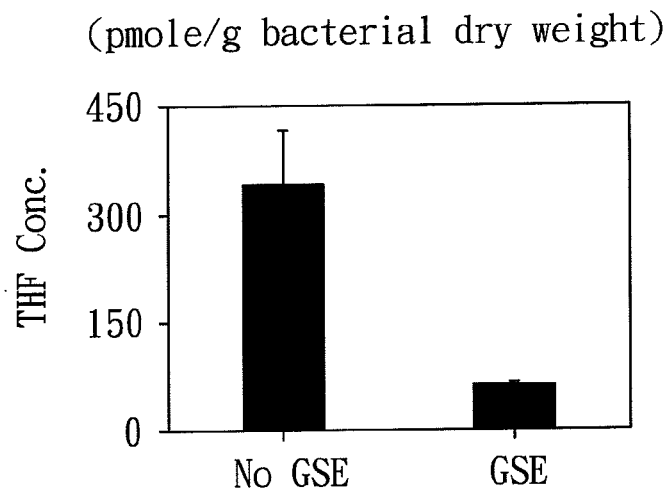

The results are shown in FIG. 3. In FIG. 3, (A) shows HPLC fluorescence and UV chromatograms of *S. aureus* and solid and dotted lines respectively represent without or with grapefruit seed extract (GSE), and (B) shows a bar chart of THF content. In the HPLC chromatogram, 1 represents THF, 2-Met represents 2-mercaptoethanol, and X represents an unknown compound.

Based on FIG. 3, the amount of THF in *S. aureus* treated with GSE is significantly decreased. This indicates enzymes such FDH or DHFR which mediate synthesis of THF are inhibited, resulting in a decrease in the amount of THF.

Accordingly, the present invention simultaneously employs a recombinant γ-glutamyl hydrolase (GGH) and a folate conversion enzyme together with HPLC to explicitly and accurately identify the sorts and the amounts of various folate derivatives in about 30 minutes, and thus satisfies the demand for folate detection in the industry.

Although the present invention has been explained in relation to its preferred embodiment, it is to be understood that many other possible modifications and variations can be made without departing from the spirit and scope of the invention as hereinafter claimed.

What is claimed is:

1. A method for detecting one or more folates selected from a group consisting of dihydrofolate (DHF), tetrahydrofolate (THF), 5-methyltetrahydrofolate (5-CH$_3$-THF) and 10-formyltetrahydrofolate (10-CHO-THF), comprising the following steps:
   (a) mixing a sample and an extraction buffer to form a mixture, boiling the mixture and cooling to an ambient temperature, and separating a supernatant from the mixture by centrifugation;
   (b) adding a recombinant γ-glutamyl hydrolase (GGH), reduced nicotinamide adenine dinucleoside phosphate (NADPH), and one or more folate conversion enzymes selected from a group consisting of dihydrofolate reductase (DHFR), 10-formyltetrahydrofolate dehydrogenase (FDH), and a combination of serine hydroxymethyl-transferase (SHMT) and methylenetetrahydrofolate dehydrogenase (MTD) to the supernatant to drive a reaction;
   (c) stopping the reaction; and
   (d) analyzing the reaction mixture by high performance liquid chromatography to quantify the one or more folates.

2. The method of claim 1, wherein the extraction buffer of step (a) is weakly acidic, having a pH range of 5.0 to 7.0 and contains an antioxidant.

3. The method of claim 2, wherein the extraction buffer of step (a) is 6-10 times the volume of the sample.

4. A kit for detecting folate, comprising:
   an extraction buffer;
   a recombinant zebrafish γ-glutamyl hydrolase;
   reduced nicotinamide adenine dinucleoside phosphate (NADPH); and
   dihydrofolate reductase (DHFR).

5. The kit of claim 4, wherein the extraction buffer is weakly acidic having pH range of 5.0 to 7.0 and contains an antioxidant.

* * * * *